United States Patent [19]

Müller et al.

[11] Patent Number: 4,732,687
[45] Date of Patent: Mar. 22, 1988

[54] CHROMATOGRAPHY COLUMN AND PROCESS FOR PACKING SAME

[75] Inventors: Peter Müller, Darmstadt; Werner Gunkel, Rossdrof; Günther Sättler, Reinheim; Willi Wintermeyer, Seeheim Jugenheim, all of Fed. Rep. of Germany

[73] Assignee: Merck Patent Gesellschaft mit beschrankter Haftung, Darmstadt, Fed. Rep. of Germany

[21] Appl. No.: 18,721

[22] Filed: Feb. 24, 1987

Related U.S. Application Data

[63] Continuation of Ser. No. 782,828, Oct. 2, 1985, abandoned.

[30] Foreign Application Priority Data

Oct. 2, 1984 [DE] Fed. Rep. of Germany ....... 3536095

[51] Int. Cl.$^4$ ............................................. B01D 15/08
[52] U.S. Cl. .................................. 210/656; 210/198.2; 55/67; 55/386
[58] Field of Search .................... 55/67, 386; 210/656, 210/657, 659, 198.2; 141/73, 80

[56] References Cited

U.S. PATENT DOCUMENTS

| 4,354,932 | 10/1982 | McNeil | 210/198.2 |
| 4,450,082 | 5/1984 | Tanouchi | 210/656 |
| 4,483,773 | 11/1984 | Yang | 210/198.2 |
| 4,497,711 | 2/1985 | Shepherd | 210/656 |
| 4,549,584 | 10/1985 | Mohin | 210/198.2 |
| 4,557,830 | 12/1985 | Onitsuka | 210/198.2 |

Primary Examiner—Ernest G. Therkorn
Attorney, Agent, or Firm—Millen & White

[57] ABSTRACT

Columns for high-pressure liquid chromatography utilize a tube which can be filled with a sorbent. The tube has an inlet device and an outlet device at the ends thereof and includes supporting elements therein to stabilize the sorbent packing.

5 Claims, 7 Drawing Figures

CHROMATOGRAPHY COLUMN AND PROCESS FOR PACKING SAME

This application is continuation of application Ser. No. 782,828 filed Oct. 2, 1985, now abandoned.

BACKGROUND OF THE INVENTION

(1) Field of the Invention

This invention relates to a column for high-pressure liquid chromatography, wherein the column includes a tube which can be filled with a sorbent packing and an inlet device and outlet device at the ends of the tube. The invention further relates to a process for filling such a tube with sorbent packing.

(2) Prior Art and Technical Considerations

In order to obtain columns having good resolving power, a very fine particulate sorbent material is used. For example silica gel having a particle size of about 5 to 50 $\mu$m, is introduced into the column as uniformly as possible in a tightly packed state. Filling the column is usually effected by closing the column at one end with an outlet device containing a filter element and filling the column with a suspension of the sorbent material via a filling device mounted at the other end, the sorbent material being retained by the filter element, while the carrier liquid passes through substantially unhindered. Filling is carried out under a predetermined high pressure of up to a few hundred bar, for example up to 500 to 700 bar, whereby very tight packing is achieved.

However, it is not possible to maintain the pressure on the packing when the filling device is uncoupled upon completion of the filling process. It has been found that as a result of this depressurization, there is a spring back of the packing, and the sorbent gushes out to some extent from the column tube. The solid stress built up in the filling operation is therefore reduced and, when the column is operated under a restored high pressure, collapse of the packing can result.

Numerous attempts have already been made to improve this situation. Thus, chromatography columns in which the sorbent packing is stabilized by means of a pressed-on plunger are described, for example, in German Offenlegungsschrift No. 30 21 366 and European published application No. 0,040,663. A column which has a flexible external wall whereby stabilization of the packing is achieved by radial compression of the separating column is described in German Offenlegungsschrift No. 30 00 475.

All these solutions require a considerable technical outlay. Moreover these solutions cannot ensure that a packing, once depressurized, can be brought back, by means of external pressure, into a state corresponding to the original packing density.

It is therefore necessary to provide a practical means for maintaining the solid stress built up after the column was filled and thus obtain a stable packing having long-term, separation avoiding properties.

SUMMARY OF THE INVENTION

It has now been found that the objective of maintaining solid stress build-up after filling a column can be achieved by providing internal fitments in the column, which fitments do not prevent build-up of solid stress when the column is filled while counteracting depressurization of the sorbent packing.

The invention relates, therefore, to a column for high-pressure liquid chromatography utilizing a tube which can be filled with a sorbent, wherein the tube has an inlet device and an outlet device at the ends of the tube, which invention is characterized by supporting elements provided in the tube to stabilize the sorbent packing.

The invention also relates to a process for filling a column for high-pressure liquid chromatography wherein the column is closed at one end by means of an outlet device containing a filter element and is filled under a predetermined high pressure from the other end via a filling device with a suspension of a sorbent material in a carrier liquid. The sorbent material is retained by the filter element, while the carrier liquid passes through the filter substantially unhindered. After being filled at the input side by means of an inlet device, the column is closed. Before the tube is filled, at least one supporting element is introduced into the tube to prevent the depressurization of the sorbent packing on completion of the filling operation.

The invention also relates to the use of column of this type in high-pressure liquid chromatography.

The main advantage of the column configured according to the invention is that, when removing the filling device and subsequently changing the inlet and outlet devices (which for example, may be terminal screwed connections), the sorbent packing remains under the predetermined pressure. The essential factor for achieving this result is that, as a result of the supporting elements fitted inside the column tube, an adequate number of supporting surfaces against which the sorbent particles can be supported are provided within the cross-section of the column.

BRIEF DESCRIPTION OF THE DRAWINGS

Some preferred embodiments of the columns according to the invention having internally fitted supporting elements are shown in the drawings.

FIG. I shows a section through one end of a column according to the invention, containing a perforated plate as the suporting element FIG. II shows a section through the same column in the unfilled state.

Figure 1:
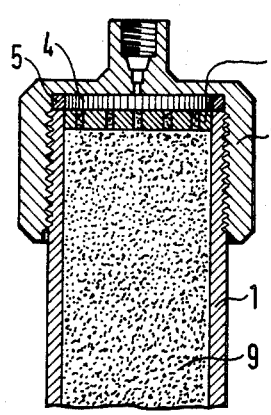
Figure 2:
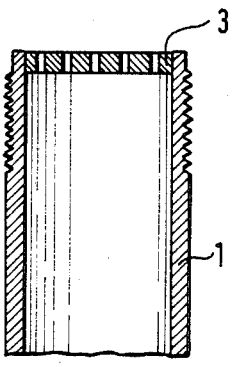
Figure 3:
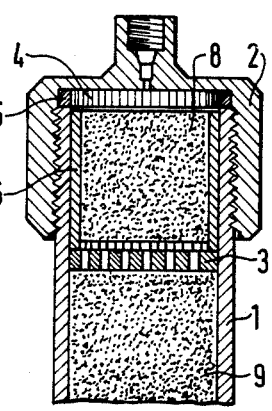
Figure 4:
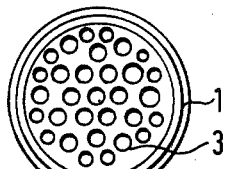
Figure 5:
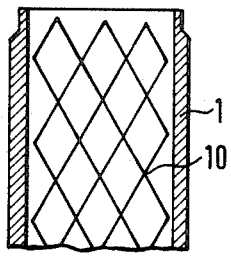
Figure 6:
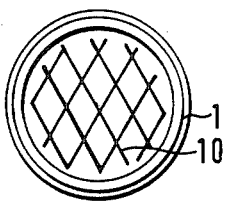
Figure 7:
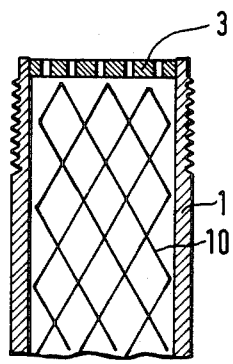

FIG. III shows a section through the inlet section of a column according to the invention having a perforated plate as the supporting element, wherein a replaceable precolumn is incorporated between the perforated plate and the end of the column.

FIG. IV is a top plan view of the device shown in FIG. II.

FIG. V shows a section through one end of a column according to the invention having a grid framework as the supporting element.

FIG. VI shows a view of the device according to FIG. V.

FIG. VII shows a section through one end of a column according to the invention, containing both a grid framework and a perforated plate as the supporting element.

DESCRIPTION OF THE PREFERRED EMBODIMENTS

In the drawings, 1 denotes the column tube, 2 denotes a reducing screwed connection and 3 denotes a perforated plate. The numeral 4 refers to a frit and 5 refers to a distributor element. The numeral 6 denotes a precolumn and 8 denotes the sorbent packing contained therein. The numeral 9 is the sorbent packing of the separating column and 10 is a grid framework.

The columns according to the invention are constructed entirely analogously to the columns known in the state or the art, that is to say they consist essentially of a column tube 1 which is filled with sorbent 9 and has inlet and outlet devices at its ends, for example reducing screwed connection 2, and also devices for distributing the streams of liquid fed through the inlet device, such as, for example, a frit 4 and a distributor element 5. As a rule, the columns are constructed in a symmetrical manner, that is to say the inlet and outlet sections of the column are identical and therefore exchangeable.

In addition, however, the columns 1 according to the invention also have at least one supporting element. This can, for example, be a perforated plate 3 shown in FIGS. I–IV and VII, which is fitted firmly into the column tube 1 and can thus resist the considerable solid pressure of the sorbent 9 in the interior of the column. A perforated plate of this type 3 is mounted on at least one end of the column and preferably on both ends. The perforated plate 3 consists of a material which is resistant in both chemical and mechanical stress. It is preferable to use perforated plates made of ceramic material, glass or stainless steel.

For filling the column, the outlet portion is closed as shown in FIG. I, while only the perforated plate 3 is attached at the inlet end, as shown in FIG. II. After placing a customary filling device on top, an emulsion of sorbent 9 is then pumped into the column, the sorbent being retained by the distributor element and the frit 4 located at the outlet end. After sufficient solid pressure has built up, the sorbent is retained by the perforated plate 3, while the carrier liquid can drain out substantially unhindered. As soon as the column has been filled with sorbent and the latter stands a few millimeters higher than the perforated plate, the filling pump can be switched off and the filling device removed. The sorbent 9 above the perforated plate can then be removed and the column closed.

In order to ensure both problem-free filling of the column and reliable stabilization of the packing, it is advantageous to choose dimensions for the apertures in the perforated plate 3 so that the free aperture is approximately within the range of 100 to 200 times the average particle diameter of the sorbent particles. Apertures of about 1 mm to about 5 mm, in particular from 1 mm to about 2 mm, are therefore preferable for the customary sorbents having diameters within the range from about 5 $\mu$m to about 50 $\mu$m.

The shape of the apertures is of only minor importance in this respect. Although circular apertures are preferred, the latter can also be, for example, oval, slit-shaped, triangular, quadrangular or polygonal. Nor do the apertures in the perforated plate 3 have to be straight as indictated in the drawings, but can also have a conical shape, so that the apertures in the lower and upper sides of the perforated plate 3 are of different sizes. In this case, the dimensions indicated above relate to the smallest dimension in each case. In the case of apertures differing from a circular shape, the optimum aperture dimension also relates to the shortest straight line through the center of the aperture.

By virtue of the relatively small apertures and the high applied pressure to which the particles of sorbent are exposed, a release of the stress on the sorbent packing 9 can only take place within a small depth of packing, so that the packing remains stable even without the application of a closure element. The user of the column can therefore exchange, in a problem-free manner, the reducing screwed connection 2 and the frit 4 and distributor elements 5 which may be present. For this reason it is advantageous to provide the perforated plate according to the invention 3 at both ends of the column.

The upper perforated plate 3 does not have to be mounted on end of the column, but can be fixed within the. column tube 1, for example approximately a few centimeters from the end of the column tube 1. This leaves space for a precolumn 6, which can also be exchanged easily.

In addition to stabilizing the packing, the perforated plate according to the invention has the advantage that turbulent flow results when the column is filled, particularly when relatively high suspension flow rates at the perforated plate 3 are used. As a result of this, an improved packing density can be achieved.

A further preferred embodiment of the invention consists in the use of a supporting framework 10 as the supporting element. This can, for example, be a framework built up in the manner of a honeycomb from a chemically and mechanically stable material, such as, for example, stainless steel or reinforced plastic, which is introduced into the empty column tube 1 before the column is filled. After the column has been filled the components of the framework are surrounded by the sorbent packing 9 over the whole length of the column. When the filling pressure is released, the packing can be supported on the framework, which prevents depressurization of the sorbent packing.

The perforated plate according to the invention 3 is very advantageous, particularly with fairly small column diameters of, for example, up to 50 or 100 mm, since it produces reliable stabilization of the sorbent packing 9 in a very simple manner. However, the greater the column diameter becomes, the more robustly must the perforated plate 3 be designed, in order to be able to resist the high internal pressure of the sorbent packing 9. The insertion of a supporting framework 10 into the column tube 1 enables the sorbent packing 9 to be stabilized without difficulty as a result of self-contained stress, even at large column diameters on the order of 500 to 1000 mm, or larger.

In addition to the preferred embodiments of the invention which have been described in detail, equivalent solutions will be accessible without difficulty to those skilled in the art on the basis of the teaching of this application. The only decisive factor in this respect is that the sorbent packing shall be distributed along the cross-sections of the column in individual segments which support one another both mutually and against one or more supporting elements and thereby can wedge and jam against one another in such a way that stabilization of the sorbent packing against pressure release is thereby achieved. It is also possible to achieve this objective without difficulty by combining several different supporting elements with one another, for example a supporting framework 10 with a perforated plate 3. It is also possible to combine a supporting element according to the invention with a conventional device for stabilizing the sorbent packing. Thus, for example, a column having a supporting framework 10 can also be equipped additionally with a compression plunger in accordance with German Offenlegungsschrift No. 3,021,366. In every case a marked improvement in the long-term stability of the sorbent packing can be observed, as a result of which the separation performance figures of the column according to the invention are improved considerably.

What is claimed is:

1. An improvement in a column used for high pressure liquid chromatography wherein the column includes a tube for containing a sorbent packing; the tube having inlet and outlet ends with coupling joints at each end and a filter at the outlet end, the improvement characterized by:

a supporting framework within the tube adjacent the ends thereof and extending longitudinally from the ends into the tube for retaining the pressurized sorbent stabilized in the tube under pressure even when a coupling joint is removed from the tube;

pressurized sorbent in the tube, the sorbent being introduced by filling the tube with the supporting framework therein under predetermined high pressure by suspending the sorbent material in a carrier liquid, the sorbent material being retained by the filter element while the carrier liquid passes through the filter element substantially unhindered, and a perforated plate positioned in at least one end of the tube outboard of the framework wherein sorbent under pressure is introduced into the tube through the perforated plate.

2. The column according to claim 1, characterized in that the perforated plate has passages therethrough wherein the diameter of the passages in the perforated plate is in the range of about 1 mm to about 5 mm.

3. The column according to claim 1, wherein the perforated plate is spaced from the end of the tube providing a space between the perforated plate and the inlet thereof, for holding a precolumn packing.

4. The column according to claim 1, characterized in that the supporting framework comprises a honeycomb-shaped metal gauze having honeycomb-shaped components, the maximum width of the individual honeycomb-shaped components being in the range of about 10 mm to about 50 mm.

5. A process for filling a column for high-pressure liquid chromatography, where the column is closed at one end by means of an outlet device containing a filter element and filled under a predetermined high pressure from the other end via a filling device by means of a suspension of sorbent material in a carrier liquid; the sorbent material being retained by the filter element while the carrier liquid passes through the filter element substantially unhindered, the column being closed after being filled on the input side by means of a inlet device, the improvement characterized by the steps of: introducing and maintaining a supporting framework within the tube adjacent the ends thereof and extending longitudinally from the ends into the tube for retaining the pressurized sorbent stabilized in the tube under pressure even when a coupling joint is removed from the tube before the column tube is filled with sorbent packing through a perforated plate secured to the column tube at the end thereof to prevent depressurization of the sorbent packing subsequent to completion of the filling operation and to maintain pressure within the column during subsequent removal of the coupling.

* * * * *